(12) United States Patent
Kuiken et al.

(10) Patent No.: US 11,612,504 B2
(45) Date of Patent: Mar. 28, 2023

(54) COMPACT WRIST ROTATOR AND FLEXOR (71) Applicant: Rehabilitation Institute of Chicago, Chicago, IL (US)

(72) Inventors: Todd Kuiken, Chicago, IL (US); Frank Ursetta, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 350 days.

(21) Appl. No.: 17/121,288

(22) Filed: Dec. 14, 2020

(65) Prior Publication Data
US 2021/0177626 A1 Jun. 17, 2021

Related U.S. Application Data (60) Provisional application No. 62/947,792, filed on Dec. 13, 2019.

(51) Int. Cl.
| | |
|---|---|
| *A61F 2/58* | (2006.01) |
| *A61F 2/70* | (2006.01) |
| *B25J 17/02* | (2006.01) |
| *A61F 2/80* | (2006.01) |
| *A61F 2/68* | (2006.01) |

(52) U.S. Cl.
CPC .............. *A61F 2/585* (2013.01); *A61F 2/68* (2013.01); *A61F 2/80* (2013.01); *B25J 17/0258* (2013.01); *A61F 2002/6836* (2013.01); *A61F 2002/701* (2013.01)

(58) Field of Classification Search
CPC ...................................................... A61F 2/585
USPC ............................................................ 623/62
See application file for complete search history.

(56) References Cited

FOREIGN PATENT DOCUMENTS

CN             102554935 A  *   7/2012   .............. B25J 9/104

\* cited by examiner

*Primary Examiner* — David H Willse
(74) *Attorney, Agent, or Firm* — Polsinelli PC (57) ABSTRACT

The present disclosure is directed to a compact wrist rotator and flexor mechanism for use with a prosthetic hand. The wrist rotator and flexor uses a set of motors to provide a driven mechanism having two degrees of freedom, a wrist rotation and a wrist flexion. The rotator uses a motor with an inverted shaft gearbox combined with a worm gear and a face gear transmission to generate continuous and non-backdrivable rotation. The rotator is integrated into a flexor that uses a lead screw acting as a linear actuator to provide strong non-backdrivable flexion and extension. Due to the arrangement of the drives, the resulting wrist rotator and flexor mechanism has a low and compact profile.

25 Claims, 10 Drawing Sheets

COMPACT WRIST ROTATOR AND FLEXOR

CROSS REFERENCE TO RELATED APPLICATIONS

The present document is a non-provisional application that claims benefit to U.S. Provisional Application Ser. No. 62/947,792, filed on Dec. 13, 2019, which is herein incorporated by reference in its entirety.

FEDERALLY SPONSORED RESEARCH OR DEVELOPMENT

This invention was made with government support under 90RE5014 and 90REGE0003 awarded by the National Institute for Disability and Rehabilitation Research (NIDRR). The government has certain rights in the invention.

TECHNICAL FIELD

The present disclosure is generally directed to prosthetic devices and more specifically to a rotator and flexor for use with a prosthetic hand.

BACKGROUND

In the field of prosthetics, a user will be less likely to use a prosthetic device if it is too heavy or bulky. Further, a prosthetic wrist device is often considered to be a supplemental device to a prosthetic hand. Because of this perspective, a wrist device is often excluded from the prosthesis to minimize its size and weight. Studies, however, have shown that wrist devices can provide benefits to prosthesis users. Specifically, the functionality of a prosthetic device for the upper limb may be increased by incorporating an additional degree of freedom provided by a wrist device. By making a wrist device lighter and more compact, there is a higher likelihood that it will be incorporated into a prosthesis, thereby increasing the chances that the user will use the device on a regular basis and regain the ability to do various tasks.

DETAILED DESCRIPTION

Turning to the drawings, wherein like reference numerals refer to like elements, the present disclosure is illustrated as being implemented in a suitable environment. The following description is based on embodiments of the claims and should not be taken as limiting the claims with regard to alternative embodiments that are not explicitly described herein.

Figure 1:
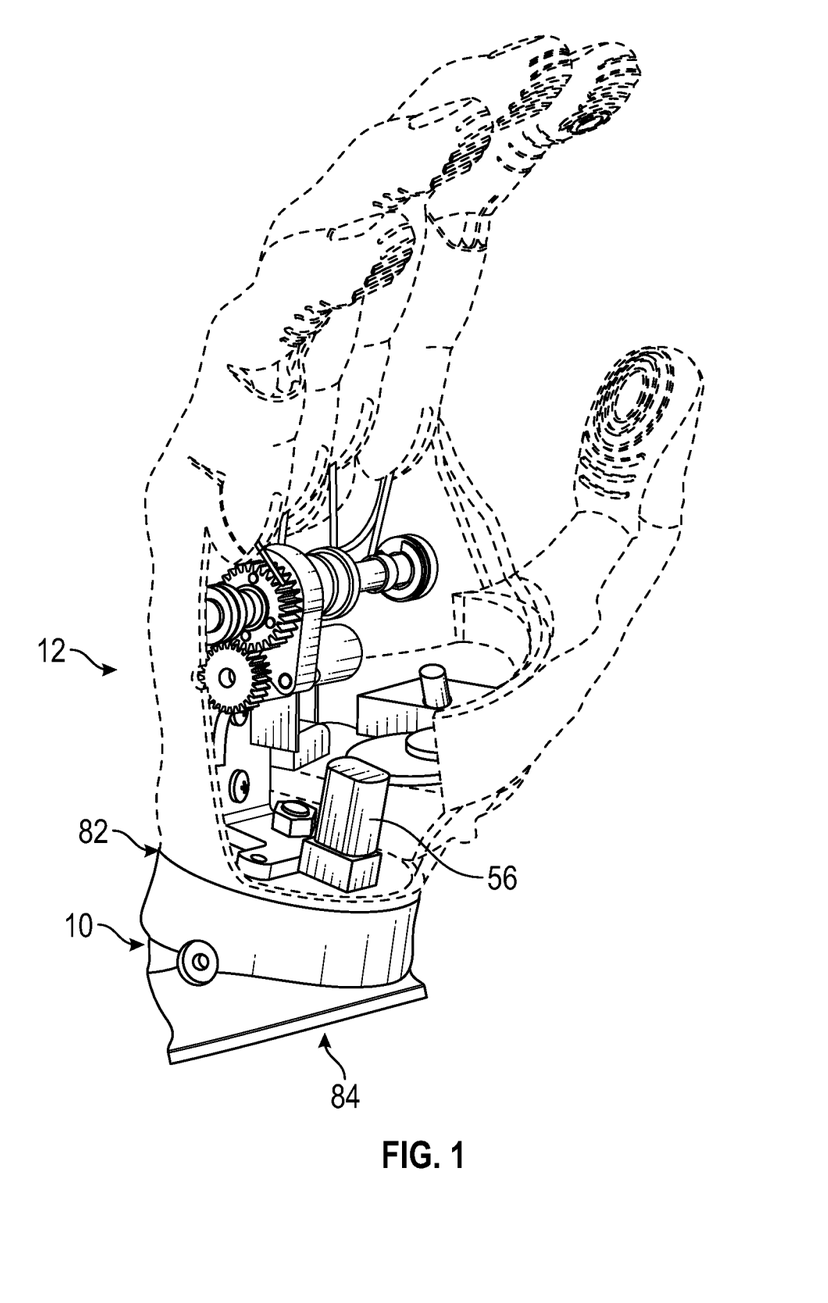
FIG. 1 is a perspective view of a wrist rotator and flexor attached to a prosthetic hand and showing a flexor motor within the prosthetic hand.

A compact wrist rotator and flexor device or mechanism 10 of the present disclosure is intended to be used with a prosthetic hand 12, as shown in FIG. 1. As illustrated, the prosthetic hand 12 is mounted to a distal end 82 of the rotator and flexor mechanism 10 by a suitable fastening means (not shown) such as a standard bolt or another suitable fastening means. An opposite proximal end 84 of the rotator and flexor mechanism 10 is attached to a forearm socket of a user (not shown) by a suitable fastening means such as a bolt or a lamination collar.

Figure 2:
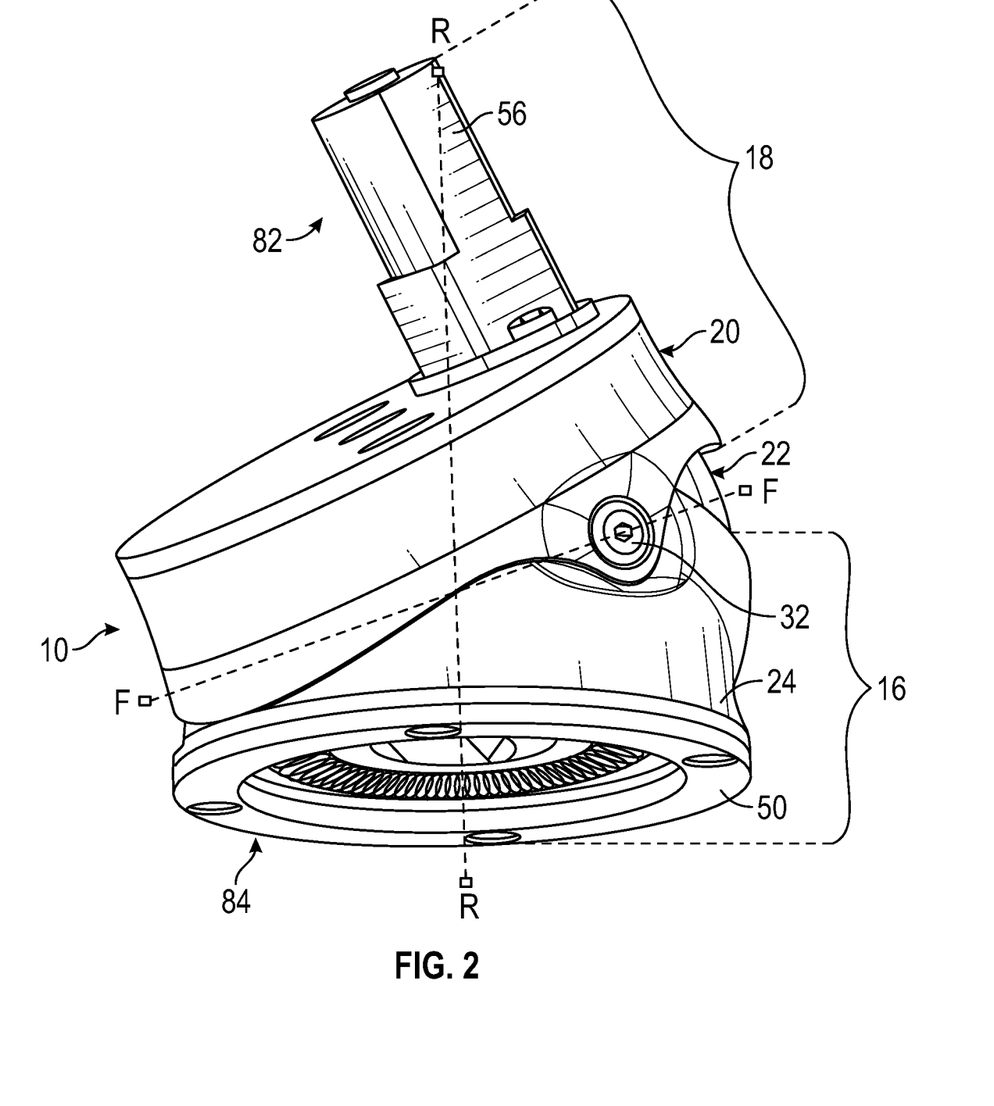
FIG. 2 is a perspective view of the wrist rotator and flexor of FIG. 1 showing flexor and rotator axes of rotation.

As shown in FIG. 2, the wrist rotator and flexor mechanism 10 includes a rotator 16 in operative association with a flexor 18. The rotator 16 allows rotation of the attached prosthetic hand 12 about an axis that would align with a forearm. The flexor 18 allows rotation of the attached prosthetic hand 12 about an axis that is orthogonal to the forearm axis. The mechanism 10 has three covers or housings, a top (or distal or flexor) housing 20, a middle housing 22, and a bottom (or proximal or rotator) housing 24, which can be seen in FIGS. 2 and 4. (The terms "proximal" and "distal" are with respect to the body of the user of the prosthesis). All three of these housings 20, 22 and 24 are operable to pivot about a single horizontal axis F-F, which also acts as a center of rotation for the flexor 18. The mechanism 10 also defines a vertical axis R-R, which is orthogonal to the flexor axis F-F. The rotator 16, specifically a face gear 42 defined by the rotator 16 (also known as a crown gear), discussed below and shown in FIG. 4, causes the rotator 16 to rotate about the vertical axis R-R.

Figure 4:
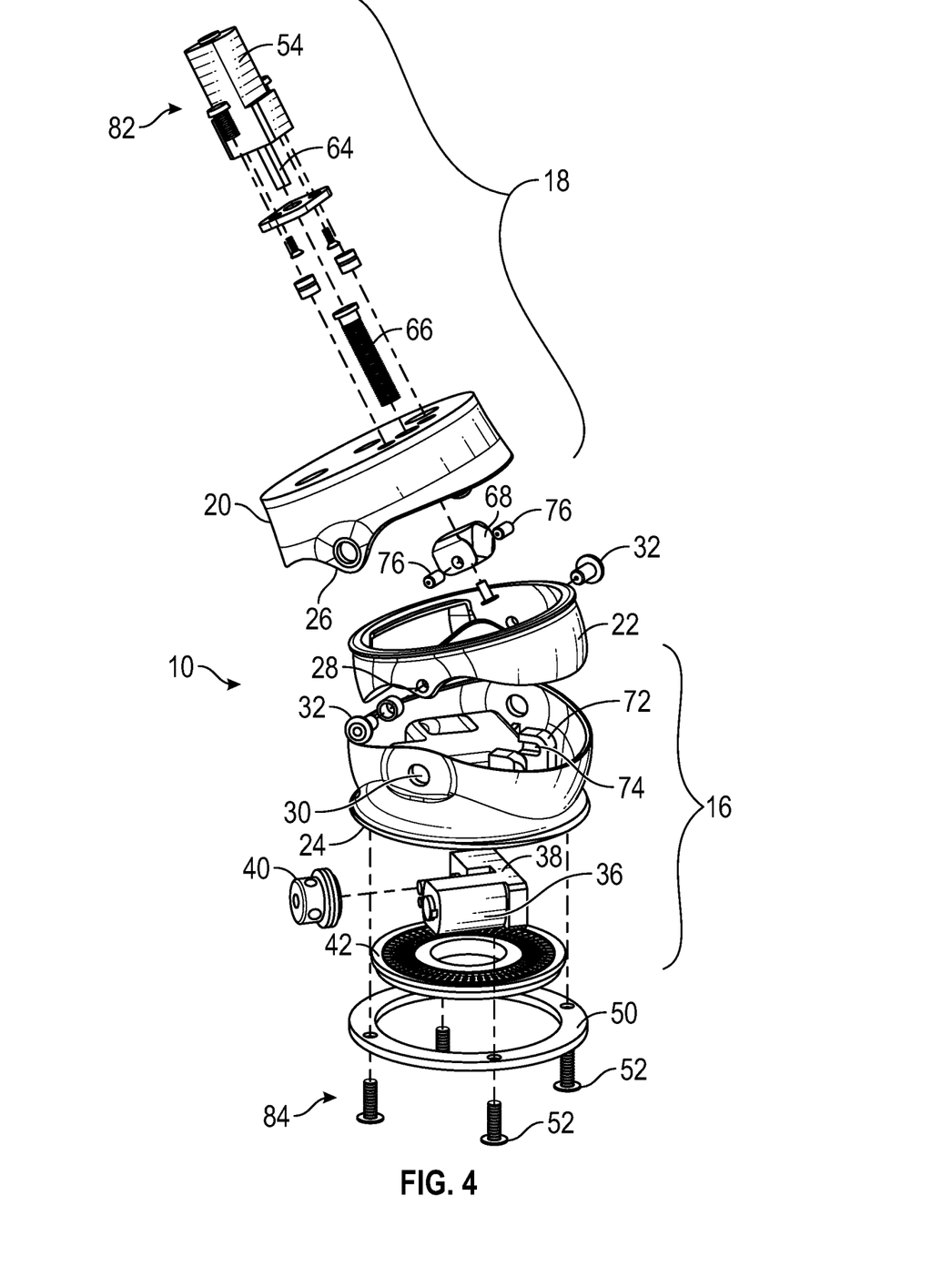
FIG. 4 is an exploded view of the wrist rotator and flexor of FIG. 1.

In order to enable the pivoting of the housings 20, 22, and 24, each housing 20, 22, and 24 is provided with a respective set of openings 26, 28, and 30 on opposite sides, as shown in FIG. 4. The device 10 is further provided with a pair of pins 32. Once the housings 20, 22, and 24 are placed in the operative arrangement where middle housing 22 is positioned between distal housing 20 and proximal housing 24 (as shown in FIG. 2), each pin 32 extends through each opening of the set of openings 26, 28, and 30 on each side of the housings 20, 22 and 24. The presence of the pins 32 allows the housings 20, 22, and 24 to pivot with respect to one another along the horizontal F-F axis.

Figure 3:
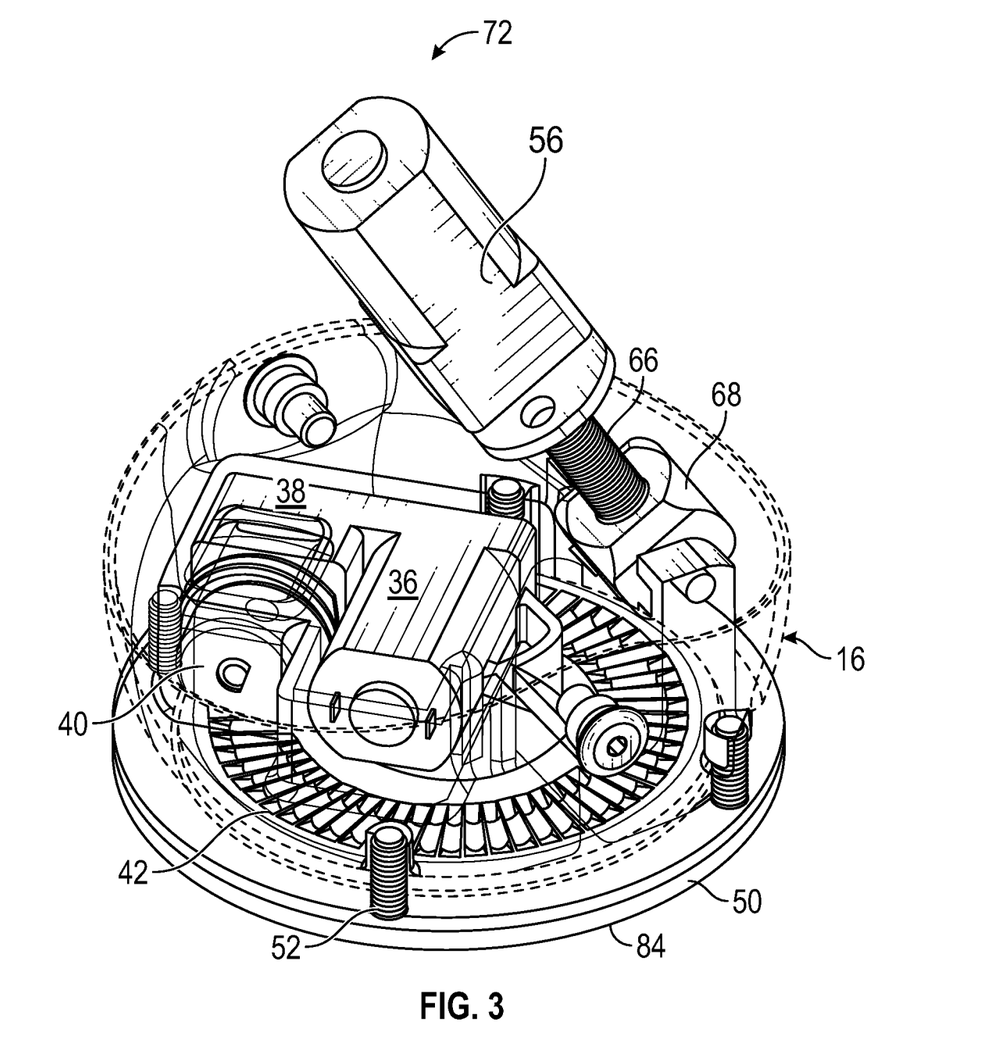
FIG. 3 is a perspective view of the wrist rotator and flexor of FIG. 1 shown with a top and middle (distal) housings removed and a bottom (proximal) housing shown transparent, thereby exposing a rotator motor within.
Figure 5:
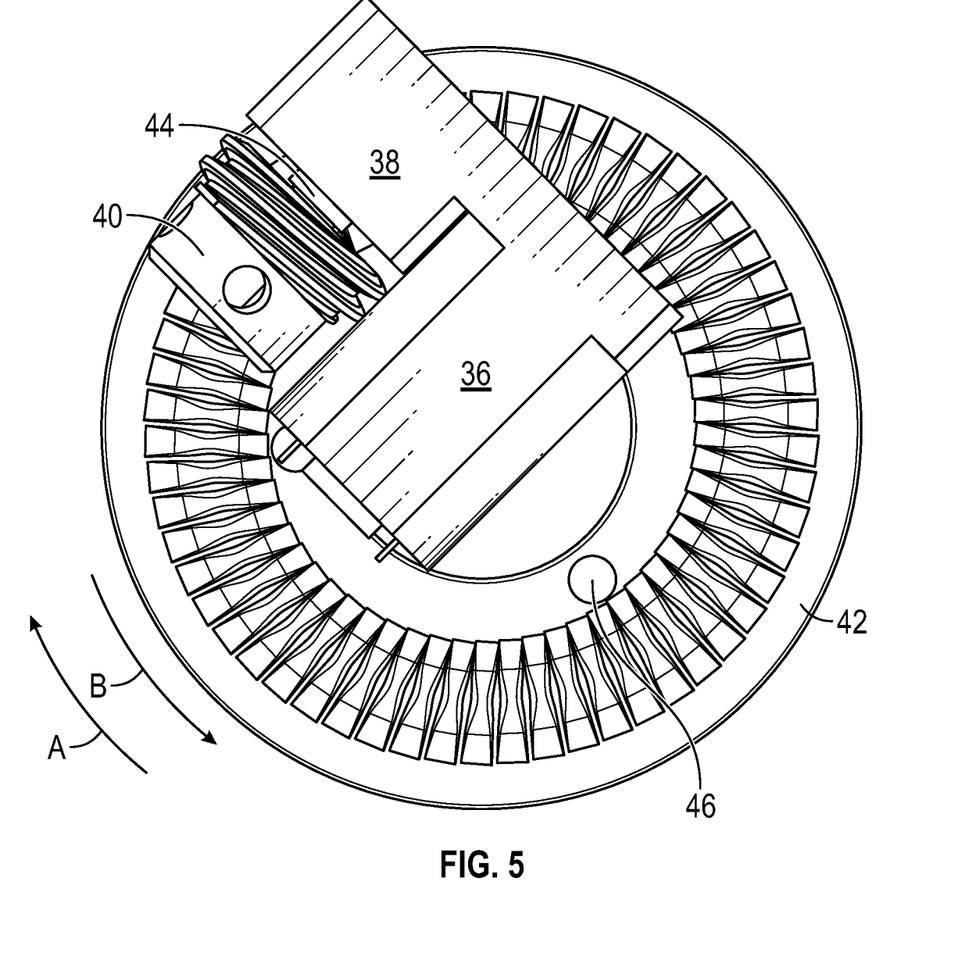
FIG. 5 is a top view of the rotator of FIG. 1 showing only the rotator motor, a worm gear and a face gear.

As can be seen in FIGS. 3 and 5, the rotator 16 includes a rotator motor 36 mounted within the bottom housing 24 at proximal end 84 of the rotator and flexor mechanism 10. The rotator motor 36 can be off-the-shelf; one suitable motor is from Uxcell DC (12V 300 rpm), model GA1024-N20. Referring directly to FIG. 5, the rotator motor 36 includes an inverted shaft gearbox 38 that drives a worm gear 40 by shaft 44, which in turn engages with face gear 42. The worm gear 40 interacts with face gear 42 to generate continuous and non-backdrivable rotation in either a clockwise direction A or a counterclockwise direction B relative to the rest of the mechanism 10. The worm gear 40 and the face gear 42 can be driven in either direction by the motor 36 so that the wrist can be rotated in either direction, but is non-backdrivable by external forces. The inverted shaft gearbox 38 allows the rotator motor 36 to drive a shaft 44 that is parallel, but offset and reversed from the motor itself, as seen in FIG. 5. Due to this arrangement, the rotator motor 36 takes up a minimal amount of space while still providing a necessary amount of torque. Thus, a diameter of face gear 42 can be as small as a diameter of an associated forearm socket (not shown) due to the reduced amount of space taken up by the arrangement of the rotator motor 36, inverted gearbox 38 and gearing arrangement including the worm gear 40 and the face gear 42. This arrangement also allows the shaft 44 to be positioned adjacent to an outer periphery of the bottom housing 24 (FIG. 4) and maximize a torque transferred to the rotating output, the face gear 42, as described below. With force being held constant, the torque increases as the distance from the center of rotation increases.

Figure 6:
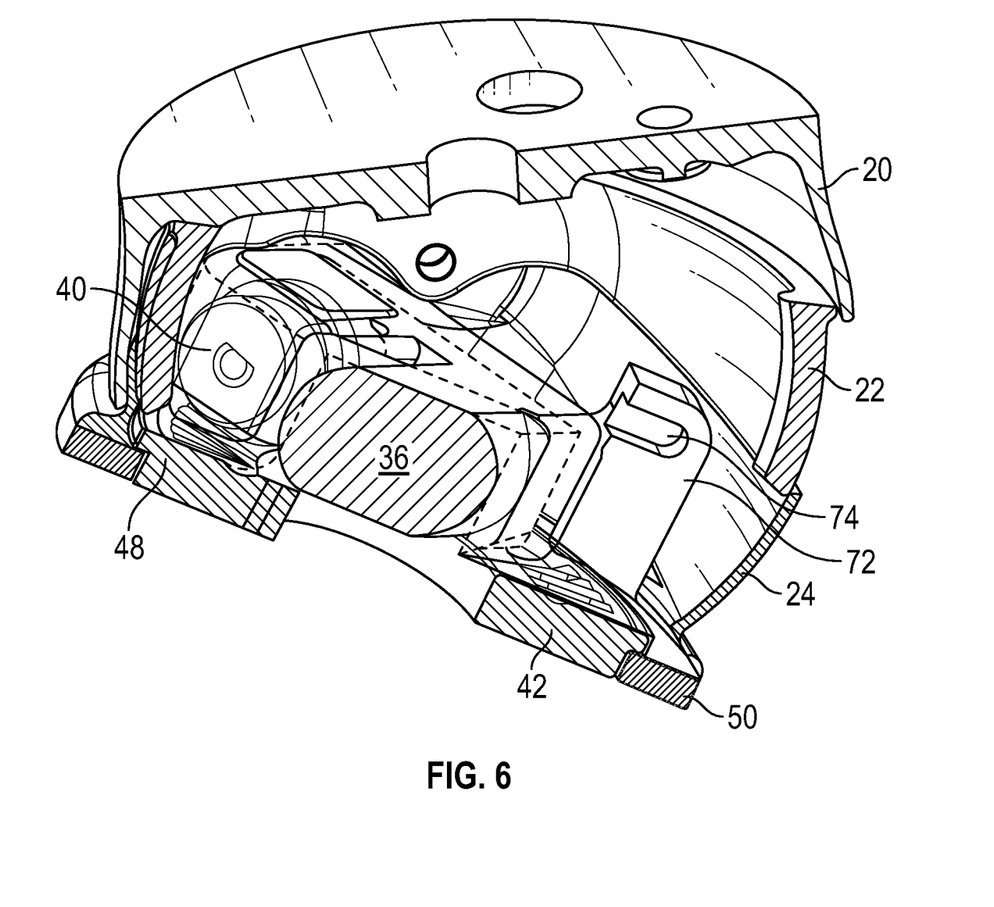
FIG. 6 is a cross sectional view of the wrist of FIG. 1 showing a lip of the face gear sandwiched between the bottom housing and a ring.

Worm gear 40 is mounted to the shaft 44 and includes a threaded portion for engagement with face gear 42, which acts as the output for the rotator 16 and would be connected to the forearm socket by any suitable fastening means. The fastening means (not shown) would connect the forearm socket to the face gear 42 via one or more fastener openings 46 provided about the center opening of the face gear 42, the fastener openings 46 shown in FIG. 5. As shown in FIG. 6, the face gear 42 includes a lip 48 that is sandwiched between the bottom housing 24 and an outer ring 50. The outer ring 50 in turn is mounted to the forearm socket (not shown) by a suitable mounting means, such as fasteners, a lamination collar or some other mounting method. The outer ring 50 is also provided with a number of fasteners 52 for mounting the outer ring 50 to the bottom housing 24. By being sandwiched between the bottom housing 24 and the outer ring 50, the face gear 42 is free to rotate about the vertical axis R-R, but is prevented from being detached from the wrist device 10 itself. The outer ring 50 also acts on or forces the face gear 42 to maintain continual contact with the threaded portion of the worm gear 40. Since the forearm socket cannot rotate, the rotation of the face gear 42 causes the housings 20, 22, and 24 and everything attached thereto, including the prosthetic hand 12, to rotate.

The worm gear 40 to face gear 42 transmission further increases the output torque of the motor 36 by providing a high gear ratio. In one particular embodiment, every rotation of the worm gear 40 rotates the face gear 42 by 6.2°. The specific gear ratio, however, may vary depending upon both a size (circumference) of the worm gear 40 and a number of teeth on the face gear 42 that engage the threaded portion of the worm gear 40. In some embodiments, the gear ratio must be such that the wrist rotator 16 has high torque and relatively slow rotation, which is optimal. A low profile of the face gear 42 combined with the orientation of the rotator motor 36 allows the rotator 16 to be compact.

The worm gear 40 transmission has the added benefit of making the entire system non-backdriveable, which is also highly desirable in a wrist rotator. That is, the motor 36 can drive the face gear 42 in a clockwise or counterclockwise direction, but attempting to manually rotate the face gear 42 does not cause the motor 36 to backdrive. Instead, the worm gear 40 mechanism prevents unintentional counter-rotation. This allows the user to grasp heavy objects without fear that the motor 36 driving the wrist rotator will rotate backwards under the load resulting from the objects.

Figure 7:
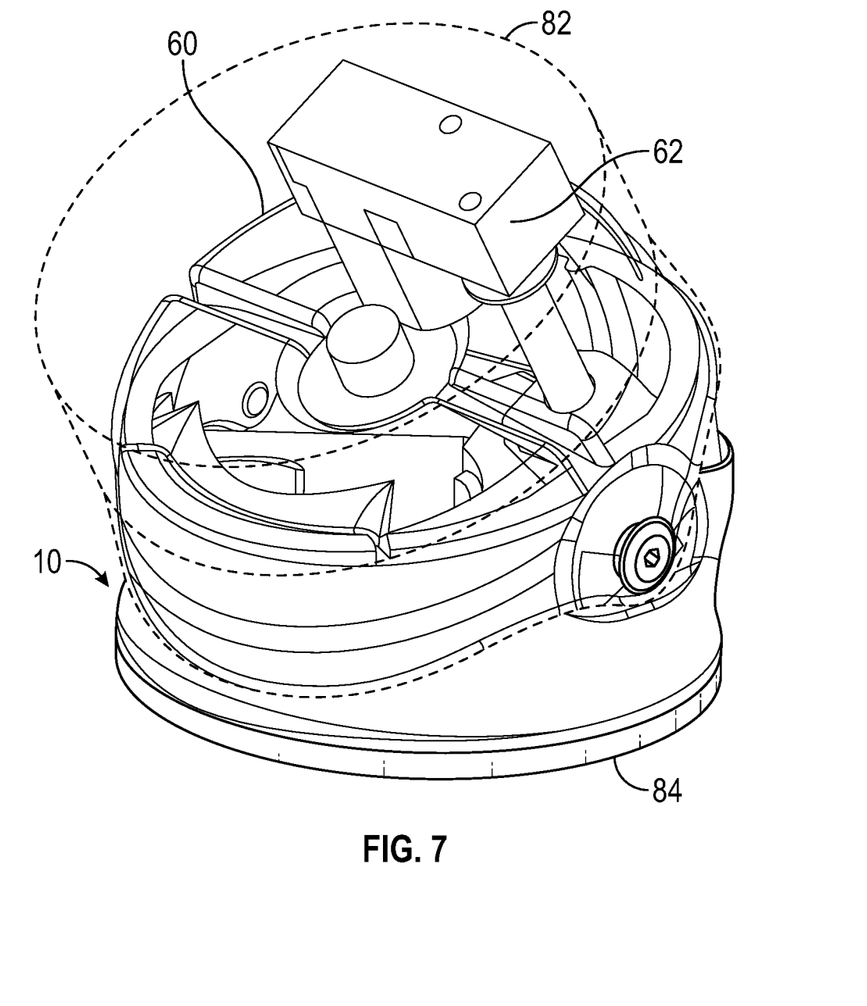
FIG. 7 depicts an alternate embodiment of the wrist rotator and flexor showing a motor with an inverted gearbox housing positioned within the upper housing and driving a lead screw.
Figure 8:
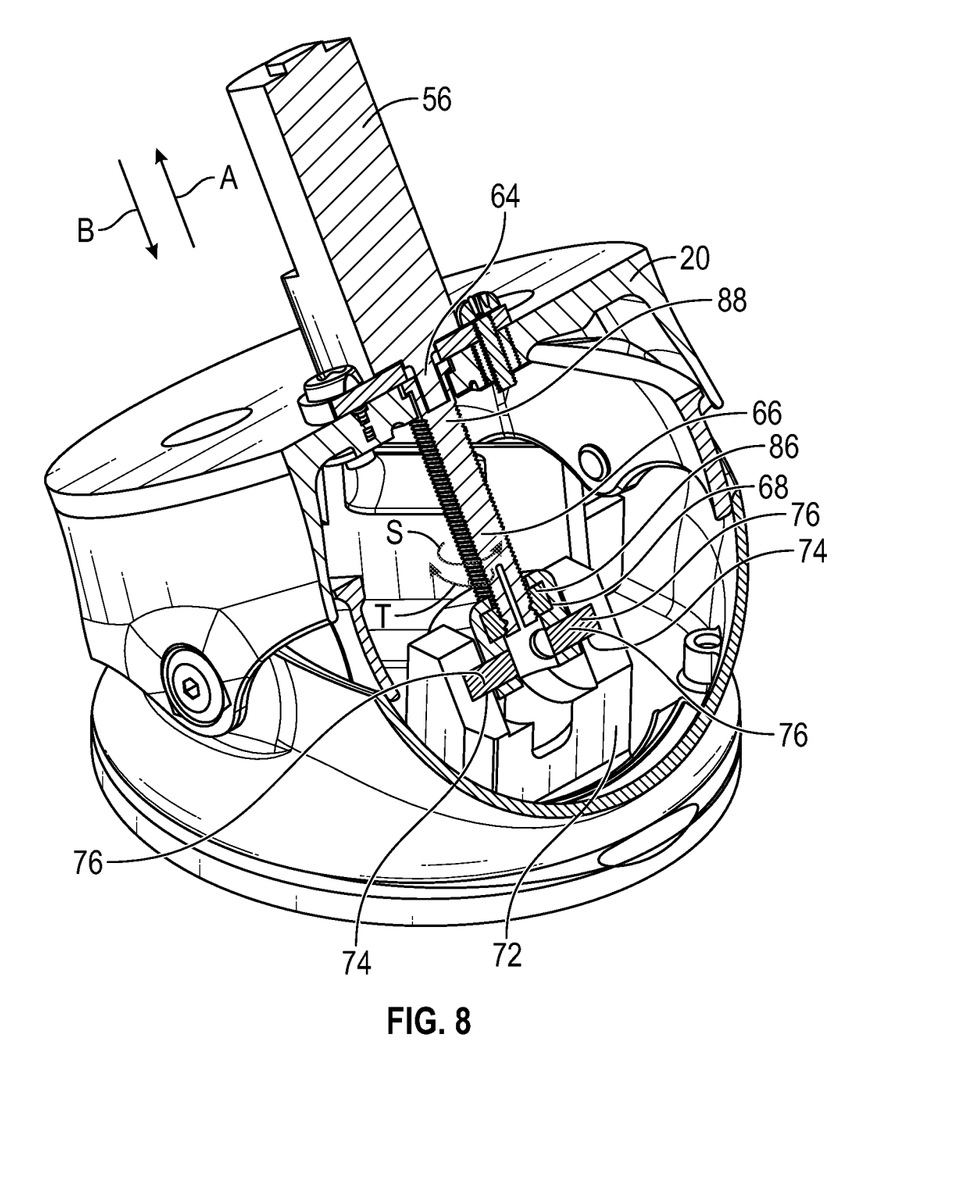
FIG. 8 is a cross sectional view of the wrist rotator and flexor of FIG. 1 showing the lead screw engaging with a nut and a plurality of pins connecting to the bottom housing.

The rotator 16 is integrated into the flexor 18 that uses a lead screw 66, acting as a linear actuator, to provide strong non-backdrivable flexion and extension. As shown in FIGS. 1 and 2, the flexor 18 is provided with a flexor motor 56. The flexor motor 56 may be mounted to the top housing 20, which is on the distal end 82 of the wrist device 10. As shown in FIG. 1, flexor motor 56 protrudes above the top housing 20 of the wrist device 10 and within the prosthetic hand 12. It should be understood that the flexor motor 56 can alternately be arranged to remain completely within the wrist device 10. Referring to FIG. 7, an alternate embodiment of wrist device 10' includes a flexor motor 60 coupled to an inverted gearbox 62 similar to that of the rotator motor 36. Other than the motor 60 and the inverted gear box 62, the remainder of the wrist device 10' remains the same as device 10. This alternate embodiment, however, results in the overall length of the wrist device 10' being about 9 mm longer than the device 10.

Referring to FIGS. 8 and 9A-E, in some embodiments of device 10, flexor motor 56 is an off-the-shelf geared motor with an output shaft 64 of the flexor motor 56 being coaxial with a rotor (not shown) of flexor motor 56. A lead screw 66, including a proximal end 86 and a distal end 88, is engaged with the output shaft 64 of the flexor motor 56 by the distal end 88. The proximal end 86 of the lead screw 66 engages a nut 68, the nut 68 being positioned to one side of the bottom housing 24 away from the center, as illustrated. This arrangement of the nut 68 within the bottom housing 24 creates a variable angle θ between a horizontal plane Q defined by the bottom housing and an axis R defined by the lead screw 66. The nut 68 is prevented from rotating due to its engagement with the bottom housing 24, illustrated in FIG. 8. As lead screw 66 is rotated in a first rotational direction S or an opposite second rotational direction T, the nut 68 is driven upward in a first axial direction A or downward in an opposite second axial direction B on the lead screw 66, thereby creating linear motion. The linear motion pulls or pushes the bottom housing 24 upward or downward, respectively, with respect to the top housing 20. As detailed in FIGS. 8 and 9 and as discussed, the lead screw 66 engages the nut 68 that is connected to the bottom housing 24. Specifically, the bottom housing 24 is provided with a mounting 72 having a slot 74 on either side. The nut 68 is provided with nut pins 76 extending from each side of the nut 68. Each nut pin 76 is captured within a respective slot 74 of the mounting 72. The rotation of the lead screw 66 would cause rotation of the nut 68 if unrestrained, but since the nut 68 is captured by the mating of the nut pins 76 within the slots 74, the rotation of nut 68 is translated into linear movement along the lead screw 66, thereby resulting in linear movement of the bottom housing 24 in the first axial direction A or the second axial direction B with respect to the top housing 20.

Figure 9A:
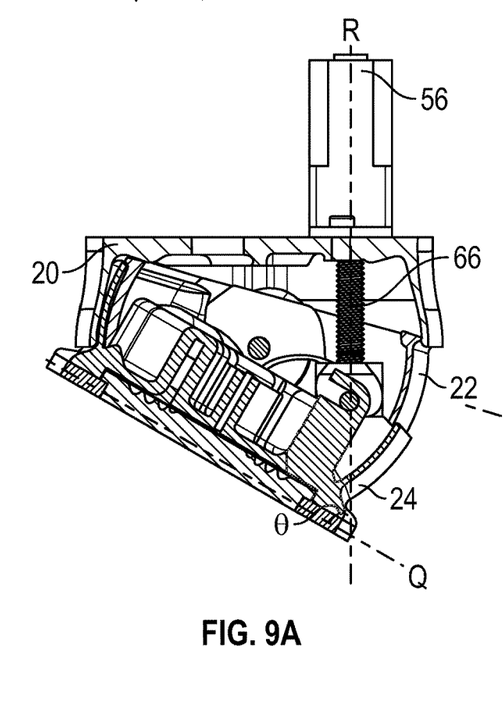
FIGS. 9A-9E are sequential cross sectional views of the wrist rotator and flexor of FIG. 1 in different stages of flexion. The pin can be seen moving within the slot of the bottom housing as the wrist flexes.
Figure 9B:
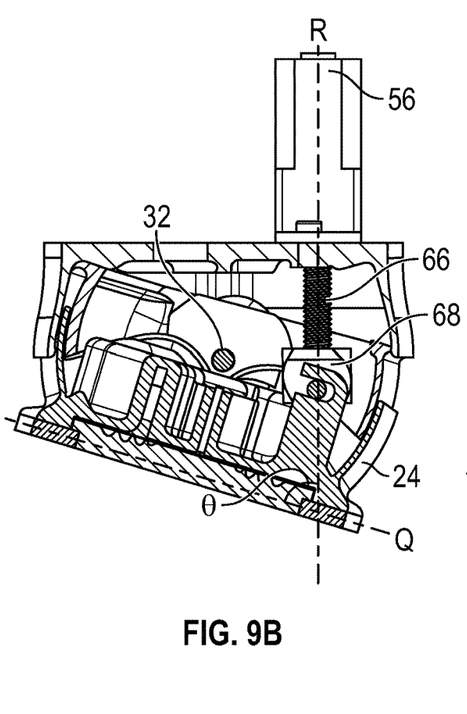
Figure 9C:
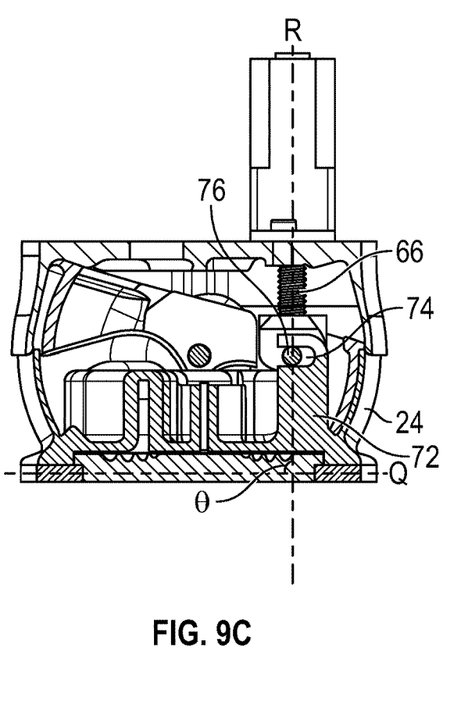
Figure 9D:
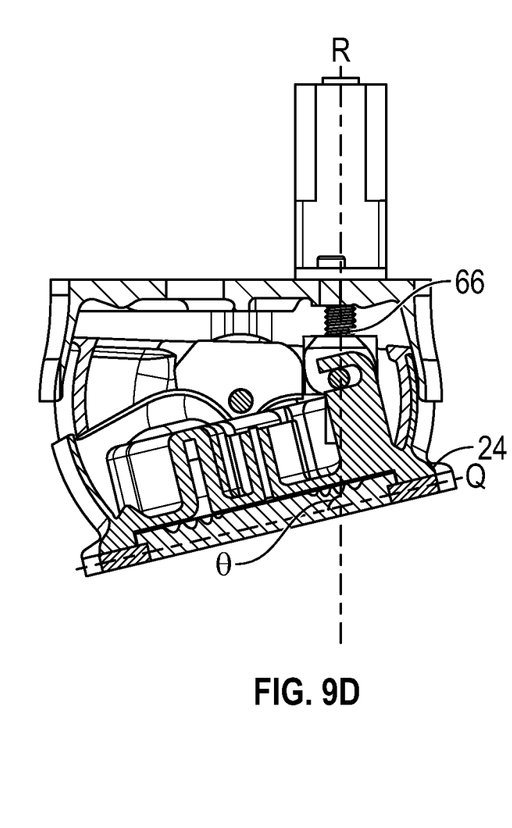
Figure 9E:
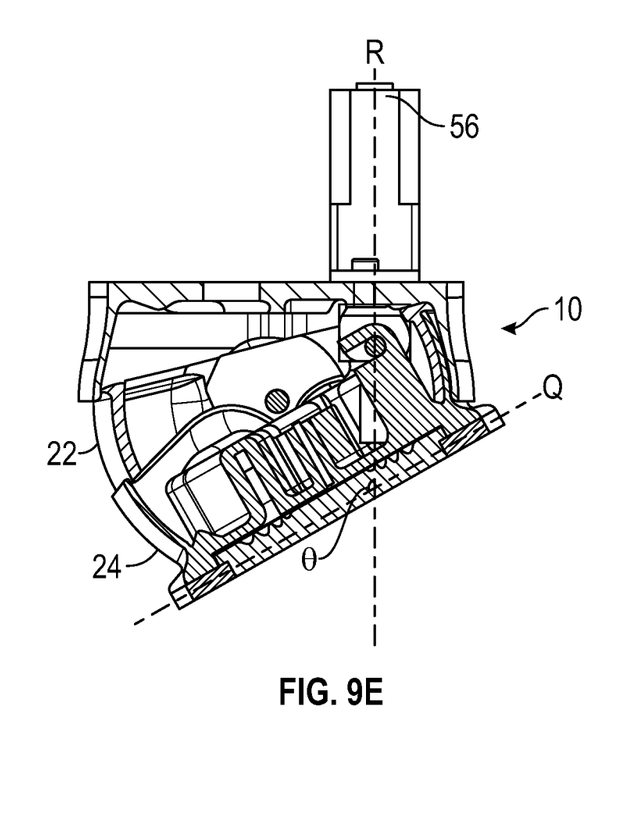

FIGS. 9(a)-(e) depict the movement of the housings 20, 22, and 24 as the lead screw 66 moves the nut 68 along in the first axial direction A or the second axial direction B as the wrist 10 flexes. (For ease of review, not all reference numerals have been provided for each view.) From FIGS. 9(a) to 9(e), the figures show the associated movement when the lead screw 66 is pulling the bottom housing 24 upward in the first axial direction A. From FIGS. 9 (e) to 9(a), the figures show the associated movement when the lead screw 66 pushing the bottom housing 24 downward in the second axial direction B. The downward movement will be further explained. Due to the rotation of the flexor motor 56, the lead screw 66 causes the nut 68 to move downward in the second axial direction B along the lead screw 66. As the nut 68 moves downward, the pins 76 move away from the end of each slot 74 of the mounting 72 (at FIG. 9d) and cause one side of the bottom housing 24 to move downward in the second axial direction B. The bottom housing 24 pivots about horizontal axis F-F (defined by pin 32) due to the pivot arrangement between the housings 20, 22 and 24 (FIGS. 9*c*, 9*b* and 9*a*). The pivoting motion of the bottom housing 24 causes the middle housing 22 to pivot as well. By the final position at FIG. 9*a*, each nut pin 76 has moved back to the end of the slot 74. Because the housings 20, 22 and 24 are forced to pivot about axis F-F, the pinned slot 74 is required to compensate for the rotation of the housings and the change in actuation radius. The combination of linear motion and pivoting causes the top and bottom housings 20 and 24 to rotate with respect to each other, which can be referred to as a "flexion" movement. The middle housing 22 serves as a cover for any gaps created by this movement.

The rotator and flexor motors 36 and 56 that control the rotator 16 and flexor 18 of mechanism 10 can be driven through numerous techniques. Wires for the motors 36 and 56 can be routed through openings in the middle housing 22 so that they are accessible at the forearm socket (not shown). Once routed, the motors 36 and 56 can be controlled by switches or through a more complex control system driven by myoelectrical signals with electrodes placed on the surface of the skin. Suitable control systems can be found at Lenzi T, Lipsey J, and Sensinger J., "The RIC arm—a small, anthropomorphic transhumeral prosthesis", IEEE/ASME Transactions on Mechatronics, 2016, and Sensinger J, Lipsey J, Sharkey T, Thomas A, Miller L A, Turner K, Ochoa J and Idstein T., "Initial experiences with the RIC arm", In Myoelectric Controls Symposium, 2014. A power source, such as batteries, to power the motors would also likely be located at the forearm socket, although other locations such as within the prosthetic hand are possible.

When the user of the prosthesis wants to rotate the wrist device 10, an appropriate switch is actuated to operate the rotator motor 36. The operation of the rotator motor 36 and the inverted gear box 38 causes rotation of the worm gear 40 and the face gear 42, thereby causing rotation of the bottom, middle and top housings 20, 22, 24 about vertical axis R-R as well as rotation of the prosthetic hand 12 carried on the top housing 20. When the user wants to flex the wrist device 10, an appropriate switch is actuated to operate the flexor motor 56. The operation of the flexor motor 56 causes rotation of the linear actuator 66 and movement of the nut 68 along the linear actuator 66. As described above, this causes the flexing of the wrist device 10. In another embodiment, the rotator 16 and the flexor 18 may be moved simultaneously.

The two drive motor mechanisms of the wrist rotator and flexor device 10 provide two degrees of freedom, thereby enabling both wrist rotation and flexion, which can be provided independently of one another. Further, the low profile of the face gear 42 combined with the orientation of the rotator motor 36, with the inverted gear box 38 and gearing arrangement 40/42, allows the rotator to be compact. In addition, because of the method of actuation of the flexor 18, the overall length of the combined rotator and flexor mechanism 10 is approximately 34 mm, which is considerably shorter than other commercially available wrist devices that vary in length from 70-75 mm. The compact design of this device may increase the likelihood of its use.

What is claimed is:

1. A wrist rotator and flexor device for use with a prosthetic hand, comprising:
   a. a rotator having a rotator motor with an output shaft capable of generating a force, an inverted gear box operatively coupled to the output shaft of the rotator motor, and gearing operatively coupled to the inverted gear box, the force generated by the rotator motor is converted by the inverted gear box and the gearing to rotational movement of the rotator along a vertical axis; and
   b. a flexor having a flexor motor with an output shaft capable of generating a force, a linear actuator operatively coupled to the output shaft of the flexor motor, the force generated from the flexor motor being translated by the linear actuator to a linear motion, which causes the flexor and the rotator to pivot with respect to one another;
   wherein the rotator and the flexor operate independently of one another.

2. The device of claim 1, wherein the gearing comprises a worm gear operatively coupled to the inverted gear box and a face gear operatively coupled with the worm gear, wherein the force generated by the rotator is provided by the inverted gear box to the worm gear, which in turn engages the face gear, thereby causing rotation of the rotator about the vertical axis.

3. The device of claim 1 wherein the inverted gear box is positioned offset from the output shaft of the rotator motor.

4. The device of claim 1 wherein the rotator is provided with a rotator outer housing and the flexor is provided with a flexor outer housing, wherein the linear actuator causes the flexor outer housing and the rotator outer housing to pivot with respect to one another.

5. The device of claim 4 further comprising a third outer housing positioned between the rotator outer housing and the flexor outer housing.

6. The device of claim 4 further comprising a first pair of openings provided on opposite sides of the rotator outer housing and a second pair of openings provided on opposite sides of the flexor outer housing and a pair of pivot members configured to be operatively coupled with the first and second pairs of openings to facilitate pivoting of the rotator outer housing with respect to the flexor outer housing.

7. The device of claim 2 wherein the face gear is located along a bottom of the rotator.

8. The device of claim 2 further comprising a ring for mounting the device to a forearm socket, the face gear being provided with a lip about its circumference that is captured between a rotator outer housing and the ring.

9. The device of claim 1 wherein the flexor is provided with a flexor outer housing and the flexor motor extends upwardly from the flexor housing and into the prosthetic hand.

10. The device of claim 1 wherein the linear actuator comprises a lead screw and is further provided with a nut that is driven in a first axial direction or a second axial direction along the lead screw.

11. The device of claim 10 wherein the rotator further comprises a rotator outer housing having a mounting, the nut being operatively coupled to the mounting of the rotator outer housing.

12. The device of claim 11 wherein the mounting is provided with at least one slot and the nut is provided with at least one pin, the at least one pin mating with the at least one slot such that movement of the nut results in movement of the rotator outer housing.

13. The device of claim 1 further comprising a proximal end and a distal end, the distal end of the device configured to be mounted to the prosthetic hand and the proximal end of the device configured to be mounted to a forearm socket.

14. A wrist prosthetic device for use with a prosthetic hand, comprising: a rotator having a rotator motor, an inverted gear box and a gearing arrangement;

the rotator motor having an output shaft capable of generating a force; the inverted gear box being operatively coupled to the output shaft of the motor;

the gearing arrangement comprising a worm gear and a face gear operatively coupled to the inverted gear box, the worm gear and the inverted gear box being positioned adjacent to, parallel to and offset from the output shaft of the rotator motor;

wherein the force generated by the rotator motor is converted by the inverted gear box and the gearing arrangement to rotational movement of the rotator about a vertical axis.

15. The wrist device of claim 14 further comprising a rotator outer housing enclosing the rotator motor, the inverted gear box, and the gearing arrangement.

16. The wrist device of claim 14 further comprising:

a flexor having a flexor motor with an output shaft capable of generating a force, a linear actuator operatively coupled to the output shaft of the flexor motor, whereby when the force generated from the flexor motor is translated by the linear actuator to a linear motion, causing the flexor and the rotator to pivot with respect to one another.

17. The wrist device of claim 16 further comprising:

a rotator outer housing enclosing the rotator motor, the inverted gear box, and the gearing arrangement;

a flexor outer housing partially enclosing the flexor and mating with the rotator outer housing;

the flexor motor causing the flexor outer housing and the rotator outer housing to pivot with respect to one another.

18. The wrist device of claim 16 wherein the rotator and the flexor are configured to operate independently of one another.

19. The device of claim 17 wherein the linear actuator comprises a threaded rod and is further provided with a nut that is driven along the length of the rod.

20. The device of claim 19 wherein the rotator outer housing having a mounting, the nut being operatively coupled to the mounting of the rotator outer housing.

21. The device of claim 20 wherein the mounting is provided with at least one slot and the nut is provided with at least one pin, the at least one pin mating with the at least one slot so that any movement of the nut results in movement of the rotator outer housing.

22. The device of claim 16 wherein the flexor motor extends upwardly from the flexor and into the prosthetic hand.

23. The device of claim 14 wherein the output shaft of the rotator motor is arranged transversely to the vertical axis about which the rotator rotates.

24. The device of claim 23, wherein the inverted gearbox includes an input shaft and an output shaft, wherein the input shaft of the inverted gearbox is located adjacent to the output shaft of the rotator motor and wherein the output shaft of the inverted gearbox is oriented away from the output shaft of the rotator motor such that a torque produced by the output shaft of the inverted gearbox is opposite to a torque produced by the output shaft of the rotator motor.

25. The device of claim 24, wherein the worm gear is operatively engaged with the output shaft of the inverted gearbox and the face gear such that as the output shaft of the inverted gearbox rotates, the worm gear rotates the face gear about the vertical axis.

* * * * *